United States Patent [19]

Waycuilis

[11] Patent Number: 5,733,941
[45] Date of Patent: Mar. 31, 1998

[54] HYDROCARBON GAS CONVERSION SYSTEM AND PROCESS FOR PRODUCING A SYNTHETIC HYDROCARBON LIQUID

[75] Inventor: John J. Waycuilis, Cypress, Tex.

[73] Assignee: Marathon Oil Company, Findlay, Ohio

[21] Appl. No.: 600,565

[22] Filed: Feb. 13, 1996

[51] Int. Cl.[6] .................................................. C07C 27/06
[52] U.S. Cl. ............................ 518/703; 518/704; 252/373
[58] Field of Search ................................................ 518/703

[56] References Cited

U.S. PATENT DOCUMENTS

| | | | |
|---|---|---|---|
| 2,552,308 | 8/1951 | Buchmann et al. | 260/449.6 |
| 2,660,032 | 11/1953 | Rosenthal | 60/39.02 |
| 2,686,195 | 8/1954 | McAdams et al. | 260/449.6 |
| 3,866,411 | 2/1975 | Marion et al. | 60/39.02 |
| 3,868,817 | 3/1975 | Marion et al. | 60/39.02 |
| 3,920,579 | 11/1975 | Slater | 252/373 |
| 3,959,972 | 6/1976 | Rudolf et al. | 60/651 |
| 3,986,349 | 10/1976 | Egan | 60/39.02 |
| 4,074,981 | 2/1978 | Slater | 48/197 |
| 4,075,831 | 2/1978 | McGann | 60/39.05 |
| 4,092,825 | 6/1978 | Egan | 60/39.02 |
| 4,121,912 | 10/1978 | Barber et al. | 48/197 R |
| 4,132,065 | 1/1979 | McGann | 60/39.02 |
| 4,158,680 | 6/1979 | McGann | 261/149 |
| 4,338,292 | 7/1982 | Duranleau | 423/656 |
| 4,434,613 | 3/1984 | Stahl et al. | 60/39.07 |
| 4,618,451 | 10/1986 | Gent | 252/373 |
| 4,732,092 | 3/1988 | Gould | 110/229 |
| 4,833,170 | 5/1989 | Agee et al. | 518/703 |
| 4,946,477 | 8/1990 | Perka et al. | 48/197 R |
| 4,973,453 | 11/1990 | Agee | 422/190 |
| 5,026,934 | 6/1991 | Bains et al. | 588/314 |
| 5,177,114 | 1/1993 | Van Dijk et al. | 518/703 |
| 5,245,110 | 9/1993 | Van Dijk et al. | 585/946 |
| 5,295,356 | 3/1994 | Billy | 62/20 |

OTHER PUBLICATIONS

The Syntroleum Process; promotional flier; Aug. 1994.
"The Syntroleum Process" promotional filter, Aug., 1994.

*Primary Examiner*—Gary Geist
*Assistant Examiner*—Sreeni Padmanabhan
*Attorney, Agent, or Firm*—Jack L. Hummel; Jack E. Ebel

[57] ABSTRACT

A system and process are provided for converting a light hydrocarbon gas to a synthetic heavier hydrocarbon liquid. The system includes an autothermal reformer, a Fischer-Tropsch reactor and a Brayton cycle that are structurally and functionally integrated. In the practice of the process, a mixture of a hydrocarbon feed gas, a compressed air feed and process steam is fed to the autothermal reformer to produce a synthesis gas. The synthesis gas is fed to the Fischer-Tropsch reactor where it is catalytically reacted to produce heavy hydrocarbons. The outlet from the Fischer-Tropsch reactor is separated into water, a low heating value tail gas, and the desired hydrocarbon liquid product. The water is pressurized and heated to generate process steam. The tail gas is heated and fed with compressed air and steam to the Brayton cycle having a combustor and a series of power turbines and compressors. The tail gas and air feed are burned in the combustor to produce a combustion gas that is used to drive a power turbine linked by a shaft to an air compressor, thereby driving the air compressor. The system further includes a plurality of heat exchangers that enable heat to be recovered from the outlet of the autothermal reformer. The recovered heat is used to make the process steam as well as to preheat the hydrocarbon feed gas before it is fed to the autothermal reformer, preheat the synthesis gas before it is fed to the Fischer-Tropsch reactor and preheat the tail gas before it is fed to the combustor.

41 Claims, 3 Drawing Sheets

5,733,941

HYDROCARBON GAS CONVERSION SYSTEM AND PROCESS FOR PRODUCING A SYNTHETIC HYDROCARBON LIQUID

BACKGROUND OF THE INVENTION

1. Technical Field

The present invention relates generally to a system and process for converting a light hydrocarbon gas to a heavier synthetic hydrocarbon liquid and, more particularly, to a gas conversion system and process employing a Brayton cycle in combination with an autothermal reformer and a Fischer-Tropsch reactor.

2. Background Information

A need has long existed for converting available carbonaceous materials to scarce liquid hydrocarbon fuels having preferred performance characteristics in many applications, such as internal combustion engines, jet engines and open-cycle gas turbines. Thus, for example, U.S. Pat. No. 3,986,349 teaches a process for converting solid coal to a liquid hydrocarbon fuel by gasifying the coal to a synthesis gas, hydrogenating the resulting synthesis gas, and recovering a liquid hydrocarbon fuel from the hydrogenation product. The liquid hydrocarbon fuel is used to generate power by relatively clean combustion in an open-cycle gas turbine.

Natural gas is often plentiful in regions that are uneconomical to develop because of the lack of local markets for the gas or the high cost of transporting the gas to remote markets. An alternative is to produce the natural gas and convert it in the field to a more utilitarian liquid hydrocarbon fuel or liquid chemical product for local usage or for more cost-effective transportation to remote markets. Processes for converting light hydrocarbon gases, such as natural gas, to heavier hydrocarbon liquids are generally known in the prior art. Such processes typically involve the "indirect" conversion of methane to synthetic paraffinic hydrocarbon compounds, wherein methane is first converted to a synthesis gas containing hydrogen and carbon monoxide followed by conversion of the synthesis gas to synthetic paraffinic hydrocarbon compounds via a Fischer-Tropsch reaction. The unconverted synthesis gas remaining after the Fischer-Tropsch reaction is usually catalytically reconverted to methane via a methanation reaction and recycled to the process inlet to increase the overall conversion efficiency of the process.

Conversion of methane to a synthesis gas is often performed by high-temperature steam reforming, wherein methane and steam are reacted endothermically over a catalyst contained within a plurality of externally-heated tubes mounted in a large fired furnace. Alternatively, methane is converted to a synthesis gas via partial-oxidation, wherein the methane is exothermically reacted with purified oxygen. Partial oxidation using purified oxygen requires an oxygen separation plant having substantial compression capacity and correspondingly having substantial power requirements. Production of the synthesis gas via either of the above-recited means accounts for a major portion of the total capital cost of a plant converting methane to paraffinic hydrocarbons.

Autothermal reforming is a lower cost means of converting methane to a synthesis gas. Autothermal reforming employs a combination of partial oxidation and steam reforming. The endothermic heat required for the steam reforming reaction is obtained from the exothermic partial oxidation reaction. Unlike the above-recited partial oxidation reaction, however, air is used as the source of oxygen for the partial oxidation reaction. In addition, the synthesis gas produced by autothermal reforming contains substantial quantities of nitrogen from the inlet air. Consequently, it is not possible to recycle the unconverted components contained in the process tail gas without undesirably accumulating an excess of nitrogen within the process. Production of a nitrogen-diluted synthesis gas via autothermal reforming or partial-oxidation using air followed by conversion of the synthesis gas via a Fischer-Tropsch reaction as disclosed in U.S. Pat. Nos. 2,552,308 and 2,686,195 is, nevertheless, a useful means for obtaining synthetic hydrocarbon liquid products from methane.

U.S. Pat. No. 4,833,170 discloses another example of autothermal reforming, wherein a gaseous light hydrocarbon is reacted with air in the presence of recycled carbon dioxide and steam to produce a synthesis gas. The synthesis gas is reacted in the presence of a hydrocarbon synthesis catalyst containing cobalt to form a residue gas stream and a liquid stream comprising heavier hydrocarbons and water. The heavier hydrocarbons are separated from the water and recovered as product. The residue gas is catalytically combusted with additional air to form carbon dioxide and nitrogen which are separated. At least a portion of the carbon dioxide is recycled to the autothermal reforming step.

Although prior art hydrocarbon gas conversion processes such as disclosed in U.S. Pat. No. 4,833,170 may be relatively effective for converting the light hydrocarbon gases to heavier hydrocarbon liquids, such processes have not been found to be entirely cost effective due to significant capital equipment and energy costs attributable to compression of the inlet air. The power required to compress the inlet air represents the majority of the mechanical power required to operate the process, yet much of this power is essentially lost as unrecovered pressure energy in the residue gas from the process. The inlet air requiring compression contains substantial quantities of nitrogen that remain essentially chemically inert as the nitrogen passes through the process, ultimately exiting the process in the residue gas. Furthermore, although the residue gas has a significant chemical-energy fuel value attributable to the carbon monoxide, hydrogen, methane and heavier hydrocarbon components thereof, the residue gas is very dilute, having a low heating value that renders it very difficult and costly to recover the energy of the fuel value of the residue gas with high efficiency. Thus, it is apparent that a need exists for a more cost effective hydrocarbon gas conversion process.

Accordingly, it is an object of the present invention to provide an effective process for converting a light hydrocarbon gas to a heavier synthetic hydrocarbon liquid. It is also an object of the present invention to provide an effective system of process equipment for converting a light hydrocarbon gas to a heavier synthetic hydrocarbon liquid. More particularly, it is an object of the present invention to provide such a hydrocarbon gas conversion system and process having substantially reduced power requirements. It is another object of the present invention to provide such a hydrocarbon gas conversion system and process having substantially reduced capital equipment costs. It is yet another object of the present invention to provide such a hydrocarbon gas conversion system and process emitting substantially reduced levels of contaminants to the environment. These objects and others are achieved in accordance with the invention described hereafter.

SUMMARY OF THE INVENTION

The present invention is a system and a process for converting a light hydrocarbon gas to a synthetic heavier hydrocarbon liquid. The system is a plurality of process equipment including an autothermal reformer, a Fischer-Tropsch reactor and a Brayton cycle that are structurally and functionally integrated. In the practice of the present process, a hot mixture comprising a hydrocarbon feed gas, a compressed air feed and process steam is continuously fed to the autothermal reformer to produce a synthesis gas. The autothermal reformer outlet containing the synthesis gas is cooled and condensed to extract water therefrom. The synthesis gas is then reheated and continuously fed to the Fischer-Tropsch reactor where it is catalytically reacted to produce heavy hydrocarbons. The outlet from the Fischer-Tropsch reactor is cooled, condensed and continuously fed to product separators where the outlet is separated into water, a low heating value tail gas, and the desired hydrocarbon liquid product. The hydrocarbon liquid product is recovered from the system while the water streams from the product separators and the autothermal reformer scrubber are combined, pressurized and heated to form process steam. A portion of this process steam is returned to the autothermal reformer for the continuous production of synthesis gas.

The tail gas from the product separators is heated and continuously fed, along with a portion of the compressed air feed diverted from the autothermal reformer and the remaining portion of the process steam not returned to the autothermal reformer, to the Brayton cycle comprising a combustor and, in accordance with one embodiment, a series of power turbines and compressors. The tail gas and air feed are burned in the combustor in the presence of the process steam to produce a combustion gas. The combustor may contain a catalyst to promote the combustion reactions therein. The combustion gas is removed from the combustor and continuously conveyed to first and second stage power turbines in series, thereby driving the first and second stage power turbines. The spent gaseous mixture is then exhausted from the system. The first and second stage power turbines are linked by shafts to an air compressor and a synthesis gas compressor, respectively, thereby driving the two compressors. In an alternate embodiment, the Brayton cycle comprises a single power turbine linked by a single shaft to both the air compressor and an electrical generator. The electrical generator provides electric power to the system, specifically to an electric motor that drives the synthesis gas compressor. The electrical generator also provides electric power for export. In accordance with either embodiment, the air compressor compresses the entire air feed while the synthesis gas compressor compresses the synthesis gas being fed to the Fischer-Tropsch reactor.

The system is further provided with a plurality of heat exchangers that enable heat to be recovered from the outlet of the autothermal reformer. The recovered heat is used as noted above to heat the water streams from the autothermal reformer scrubber and the product separators, thereby providing process steam to the system. The recovered heat is also used to preheat the hydrocarbon feed gas before it is fed to the autothermal reformer and to preheat the synthesis gas before it is fed to the Fischer-Tropsch reactor. In addition, the recovered heat is used to preheat the pressurized tail gas from the product separators before it is fed to the combustor. The tail gas consequently acts as a collection medium for some of the high-grade heat energy evolved in the process.

The present system for conversion of a light hydrocarbon gas to a heavier hydrocarbon liquid has been found to be more cost effective relative to conventional conversion systems because of reduced capital equipment and operating costs. Specifically, integration of the Brayton cycle into the gas conversion system eliminates the high capital cost of providing electric- or steam-powered air compressors for compression of the air feed to the autothermal reformer and combustor. The present system also has the practical advantage of enabling commercially available gas-turbine engine packages to be utilized in the Brayton cycle. Commercial gas-turbine engine packages are available in many designs and sizes and are mass produced on a large scale to achieve a high degree of cost-effectiveness as well as rugged and reliable service.

A preferred integral Brayton cycle employs an external combustor with a conventionally designed gas-turbine engine having axial-flow inlet compressors to compress the air feed at a lower capital cost than externally-powered compressors. An alternate integral Brayton cycle eliminates the external combustor and utilizes a larger capacity gas-turbine engine having an internal air-cooled combustor. In any case, the operating cost of the integral Brayton cycle is substantially lower than the operating cost of externally-powered air compressors because the one or more Brayton cycle turbines are driven by a combustion gas formed when the low heating value tail gas is combusted with a portion of the compressed air feed. Combustion of the otherwise relatively non-combustible tail gas is enabled by preheating the tail gas with recovered waste heat from the autothermal reformer and adding the hot compressed air feed to it. Preheating the tail gas and the compressed air feed to the combustor substantially increases the flame or reaction temperature resulting from the combustion of these gases, thereby raising the enthalpy of the gas stream and the efficiency with which power may be extracted from it.

Additional operating economies are realized by the present system because the heat of compression is retained by the air feed following the compression step. Thus, the requirement to preheat the air feed to the autothermal reformer in a separate heater is eliminated. The power and energy requirements of the system are further reduced, thereby reducing operating costs, by using waste heat to effectively create superheated process steam from water generated by the system and by using waste heat to effectively preheat the gas feed to the autothermal reformer. The injection of superheated process steam into the combustor enhances the recovery of power from the process, rendering the process self-sufficient from a power standpoint, and in some cases generating excess power from the process for export. The injection of process steam also beneficially moderates temperatures and increases mass flow rates to the power turbines, thereby enabling the use of standard metallurgy in the power turbines without a substantial loss in thermal efficiency. The heat exchanger configuration of the system is also optimized to minimize the size and number of heat exchangers required by the system. The net effect of these enhancements is to maintain the capital cost of the system at relatively low levels.

It has further been found that the present system is operable in an environmentally beneficial manner to minimize the contribution of undesirable contaminants to the external environment. In particular, the water from the product separators is known to typically contain alcohols and other relatively low molecular weight liquid organic compounds that pose a disposal problem. By using this water as a source of process steam for the combustor, however, the liquid organic compounds contained therein are oxidized to carbon dioxide and steam by oxygen in the hot combustion gas and vented with the turbine exhaust to obviate the problem of disposing the liquid organics-containing water. Additionally, the presence of gaseous diluents and steam in the feed to the combustor moderates the combustion temperatures in the combustor and minimizes the formation of oxides of nitrogen, atmospheric pollutants formed in significant concentrations by conventional power-producing equipment.

The invention will be further understood from the accompanying drawings and description.

BRIEF DESCRIPTION OF THE DRAWING

The FIG. 1 is a schematic of a process of the present invention.

The FIG. 2 is a schematic of another embodiment of the process of FIG. 1 having an alternate Brayton cycle.

Figure 1:
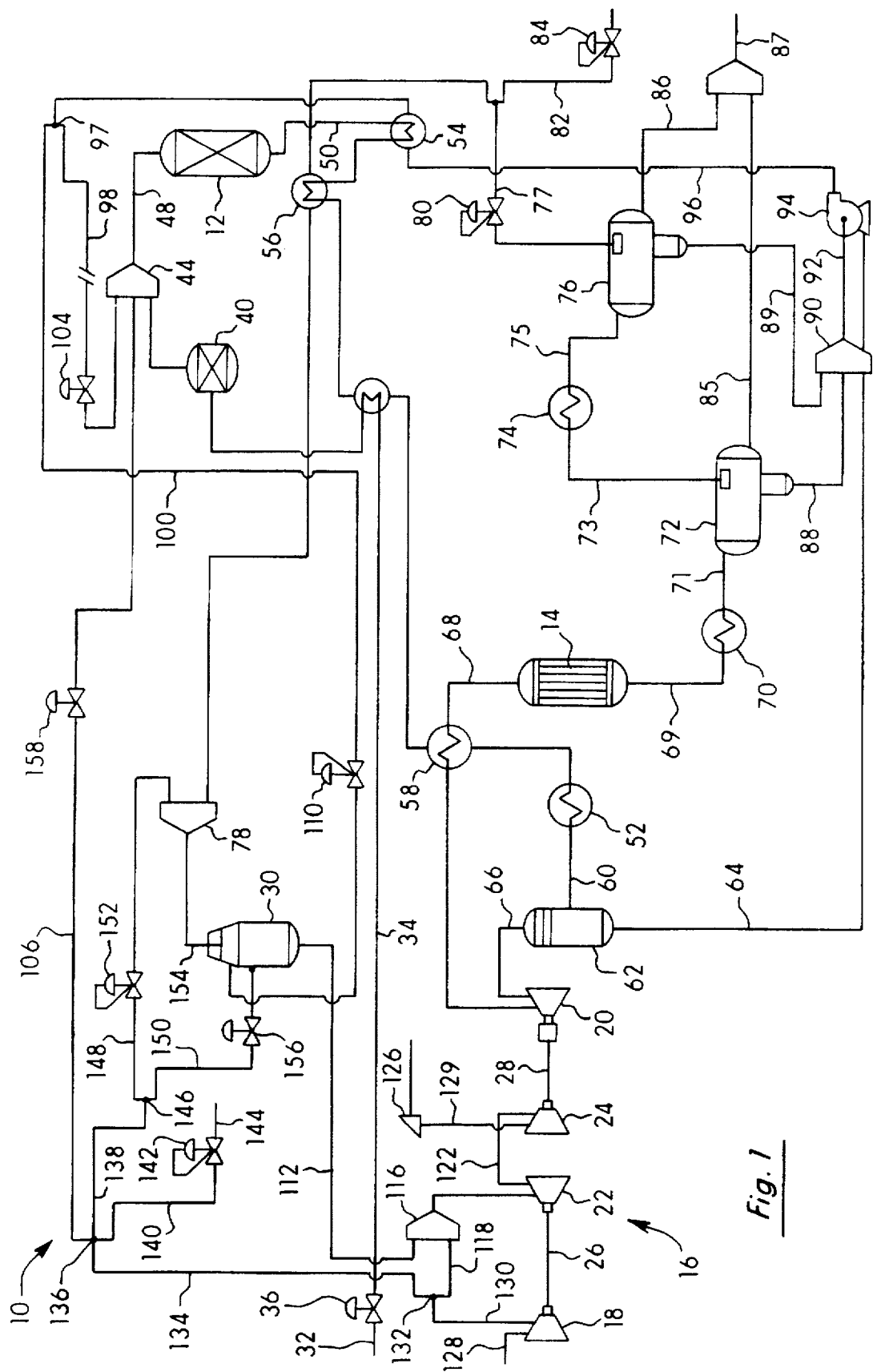
Figure 3:
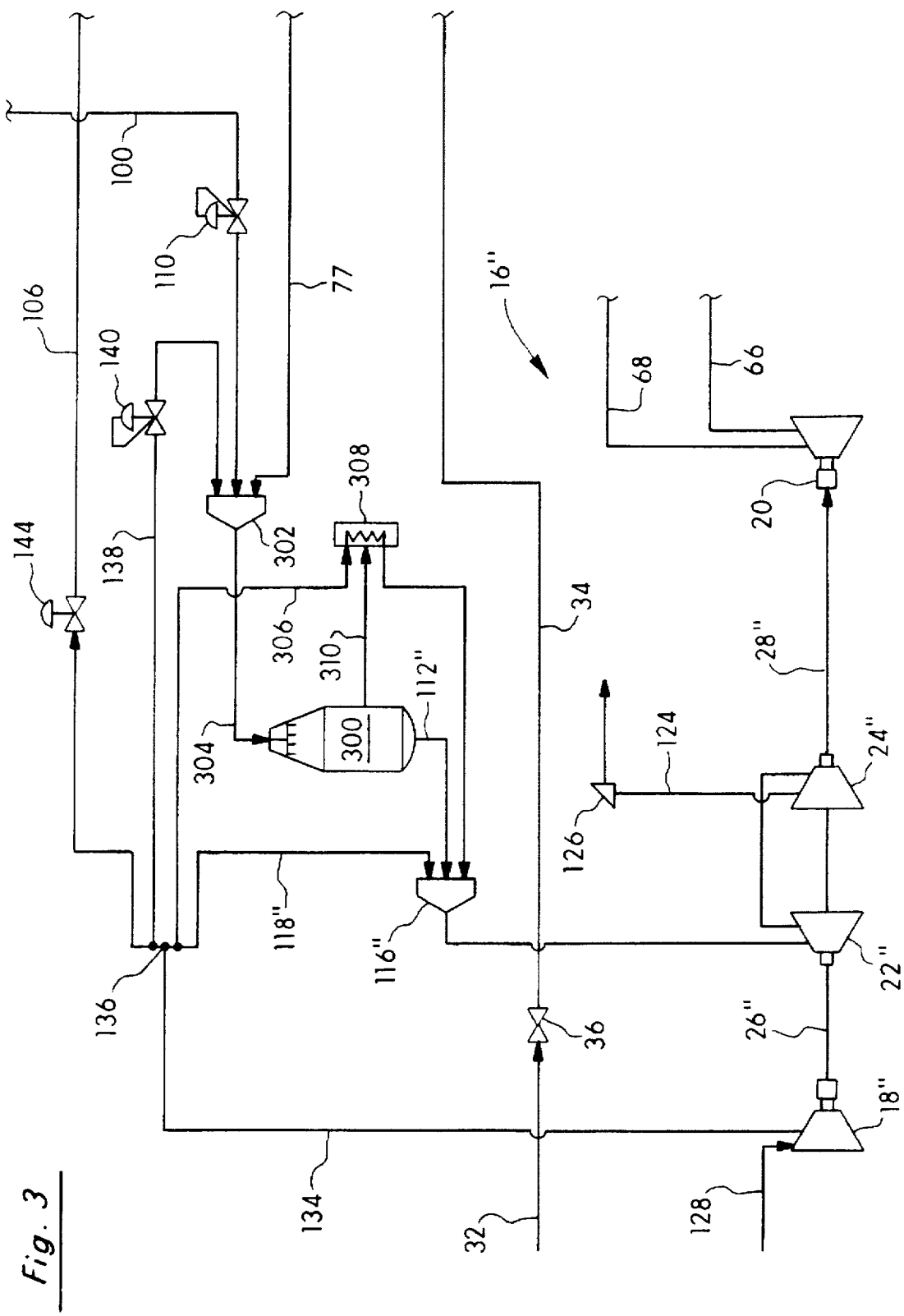

The FIG. 3 is a schematic of yet another embodiment of the process of FIG. 1 having an alternate Brayton cycle.

DESCRIPTION OF PREFERRED EMBODIMENTS

The present invention relates to a hydrocarbon gas conversion process for producing a synthetic hydrocarbon liquid. The invention further relates to a system of interconnected process equipment for practicing the hydrocarbon conversion process. The system and process are initially described hereafter with reference to the FIG. 1, in which the system is generally designated 10. It is noted that the system 10 demonstrates a preferred embodiment of an equipment configuration and process practiced therewith for a relatively small-size application, wherein operating pressure conditions are compatible with commercially available low-pressure gas-turbine/compressor sets. It is apparent to the skilled artisan from the teaching herein, however, that the system 10 can be modified within the scope of the present invention for other size applications and operating conditions.

The system 10 comprises three primary operational units. The first unit is an autothermal reformer (ATR) 12 that is provided to reform a hydrocarbon feed gas, compressed air and steam into a synthesis gas. The second unit is a Fischer-Tropsch reactor (F/T reactor) 14 that is provided to convert the synthesis gas to a synthetic hydrocarbon liquid. The third unit is a Brayton cycle 16 that is provided to compress the air feed to the ATR 12, utilizing power generated by combustion of the F/T reactor tail gas. The Brayton cycle 16 includes a pair of compressors 18, 20, a pair of power turbines 22, 24 mechanically linked by shafts 26, 28 to the compressors 18, 20, respectively, and a combustor 30 that supplies a combustion gas to the power turbines 22, 24.

More particularly, the system 10 comprises a hydrocarbon feed gas inlet 32 through which a hydrocarbon feed gas is supplied to the system 10. The hydrocarbon feed gas is typically fed through the hydrocarbon feed gas inlet 32 at a rate of about 8,000 to 12,000 $m^3$/hr, a temperature in a range of about 16° to 67° C., and a pressure in a range of about 1,000 to 10,000 kPa. The hydrocarbon feed gas is preferably a naturally-occurring, non-synthetic hydrocarbon gas produced from a subsurface formation. Among such gases, natural gas is most preferred, although other hydrocarbon feed gases have utility herein, including subquality gas containing nitrogen and/or carbon dioxide, gas derived from coal seams or gas derived from ocean hydrates. A hydrocarbon feed gas inlet line 34, having a hydrocarbon feed gas pressure control valve 36 positioned therein, connects to the hydrocarbon feed gas inlet 32 and conveys the hydrocarbon feed gas downstream in the direction of the ATR 12. Also serially positioned in the hydrocarbon feed gas inlet line 34 downstream of the hydrocarbon feed gas inlet 32 are a hydrocarbon feed gas heat exchanger 38 and an $H_2S$ removal unit 40. The hydrocarbon feed gas heat exchanger 38 preheats the hydrocarbon feed gas to a temperature in a range of about 380° to 450° C. by means of a high-temperature synthesis gas exiting the ATR 12, as described hereafter. The preheated hydrocarbon feed gas has a resultant pressure in a range of about 900 to 1,100 kPa. The $H_2S$ removal unit 40 is a zinc oxide bed that substantially removes all $H_2S$ present in the preheated hydrocarbon feed gas via chemical reaction with the zinc oxide.

The hydrocarbon feed gas line 34 extends from the hydrocarbon feed gas inlet 32 to an ATR carburetor 44. Air and stream also feed into the ATR carburetor 44 from an air and steam source described hereafter. The ATR carburetor 44 mixes the hydrocarbon feed gas from the hydrocarbon feed gas line 34 with the air and steam and an ATR inlet gas mixture line 48 exits the ATR carburetor 44 carrying the gaseous mixture comprising the hydrocarbon feed gas, air and steam (termed the ATR inlet gas mixture) from the ATR carburetor 44 to the ATR 12. The composition of the ATR inlet gas mixture is selected in accordance with the requirements of the ATR 12 and the desired composition of the final synthetic hydrocarbon liquid product. The ATR inlet gas mixture typically has a molar composition in a range of about 3.0 to 3.5 moles of air and about 0.15 to 0.30 moles of steam per mole of hydrocarbon feed gas and is supplied to the ATR 12 at a combined rate of about 35,000 to 50,000 $m^3$/hr, a temperature in a range of about 350° to 450° C., and a pressure in a range of about 900 to 1,100 kPa.

The ATR 12 is a high-temperature reactor vessel, wherein the ATR inlet gas mixture is adiabatically reacted to produce a synthesis gas containing $H_2$ and CO, preferably in a molar ratio of about 2:1, although other ratios are possible within the scope of the present invention by adjusting the ATR conditions in a manner apparent to the skilled artisan in accordance with the teaching herein. Adiabatic treatment of the ATR inlet gas mixture in the ATR 12 to produce a synthesis gas comprises partially combusting the hydrocarbon feed gas of the ATR inlet gas mixture to exothermically oxidize a portion thereof and contacting the methane component of the hydrocarbon feed gas in the ATR inlet gas mixture with steam in the presence of a steam reforming catalyst, such as nickel-containing catalysts well known in the art, to endothermically reform the methane and steam. The ATR 12 is preferably maintained at a temperature in a range of about 900° to 1,050° C. and a pressure in a range of about 900 to 1,100 kPa.

An ATR outlet line 50 removes the synthesis gas from the ATR 12 at a rate of about 45,000 to 66,000 $m^3$/hr. The synthesis gas exiting the ATR 12 preferably has a molar composition of about 2.0 moles of hydrogen per mole of carbon monoxide, a temperature in a range of about 900° to 1,050° C., and a pressure in a range of about 800 to 950 kPa. The ATR outlet line 50 conveys the synthesis gas from the ATR 12 to an ATR condenser 52. Serially positioned in the ATR outlet line 50, however, upstream of the ATR condenser 52 are a plurality of heat exchangers including a steam conversion heat exchanger 54, a separator tail gas heat exchanger 56, the hydrocarbon feed gas heat exchanger 38, and an F/T reactor feed gas heat exchanger 58. The steam conversion heat exchanger 54 utilizes the high-temperature synthesis gas exiting the ATR 12 to heat process water for steam conversion, while quenching the synthesis gas to a temperature in a range of about 500° to 650° C. The separator tail gas heat exchanger 56 utilizes the high-temperature synthesis gas to heat a tail gas exiting a product separator described hereafter downstream of the F/T reactor 14. The hydrocarbon feed gas heat exchanger 38 utilizes the high-temperature synthesis gas to heat the hydrocarbon feed gas to the ATR 12 as described above. The F/T reactor feed gas heat exchanger 58 utilizes the high-temperature synthesis gas to heat the synthesis gas to the F/T reactor 14.

The ATR outlet line 50 feeds the synthesis gas into the ATR condenser 52 at a rate of about 37,000 to 54,500 kg/hr, a temperature in a range of about 250° to 350° C., and a pressure in a range of about 600 to 700 kPa. The ATR condenser 52 cools the synthesis gas, condensing the water contained therein. A condenser outlet line 60 conveys the resulting mixture of cooled synthesis gas and water from the ATR condenser 52 to a scrubber 62 where the water is separated from the synthesis gas. A scrubber water outlet line 64 withdraws the water from the bottom of the scrubber 62 for conversion to steam and return to the system 10. A scrubber gas outlet line 66 withdraws the cooled synthesis gas from the top of the scrubber 62 at a rate of about 42,000 to 63,000 m³/hr, a temperature in a range of about 20° to 50° C., and a pressure in a range of about 500 to 600 kPa. The scrubber gas outlet line 66 conveys the cooled synthesis gas to the synthesis gas compressor 20 of the Brayton cycle 16.

The synthesis gas compressor 20 compresses the synthesis gas to a pressure in a range of about 2000 to 3000 kPa and a temperature in a range of about 150° to 250° C. The synthesis gas compressor 20 is driven by the shaft 28 connected to the second stage power turbine 24 which is driven by means described hereafter. An F/T reactor inlet line 68 conveys the compressed synthesis gas from the synthesis gas compressor 20 to the F/T reactor 14 at a rate of about 35,000 to 52,000 kg/hr. The F/T reactor feed gas heat exchanger 58 described above preheats the compressed synthesis gas to within a temperature range of about 200° to 240° C. and a pressure range of about 2,000 to 2,800 kPa before the synthesis gas is fed to the F/T reactor 14. Fischer-Tropsch reactors are generally known in the art and the present F/T reactor 14 is selected by the skilled artisan in accordance with the teaching provided herein to satisfy the performance requirements of the present process. In accordance with such teaching the F/T reactor 14 can be one or more packed tubular reactors in series or alternatively the F/T reactor 14 can be a fluidized bed reactor. In any case, the F/T reactor 14 is preferably charged with a cobalt-containing catalyst and is maintained at nearly isothermal conditions by means such as externally cooling the F/T reactor 14 with boiling water or some other cooling medium to remove the exothermic heat of reaction. The temperature of the F/T reactor 14 is preferably in a range of about 200° to 235° C. and the pressure is in a range of about 1,600 to 2,800 kPa, thereby reacting the CO and $H_2$ of the synthesis gas to form water and heavy hydrocarbons therefrom.

An F/T reactor outlet line 69 withdraws the entire F/T reactor product, comprising a mixture of light and heavy hydrocarbons, as well as nitrogen and steam, from the F/T reactor 14 at a rate of about 35,000 to 52,000 kg/hr, a temperature in a range of about 200° to 240° C., and a pressure in a range of about 1,600 to 2,800 kPa. The molar conversion of carbon monoxide in the F/T reactor 14 to hydrocarbon products (methane and heavier hydrocarbons) is preferably about 90%. The F/T reactor outlet line 69 feeds the F/T reactor product to an F/T reactor cooler 70 where the F/T reactor product is cooled to a temperature in a range of about 60° to 100° C., depending on the amount of waxes formed, and a pressure in a range of about 1,500 to 2,800 kPa, thereby condensing the F/T reactor product to form a first product mixture comprising a liquid portion and a vapor portion. The liquid portion of the first product mixture contains heavy hydrocarbon liquids and water.

An F/T reactor cooler outlet line 71 conveys the first product mixture to a heavy product separator 72 where the vapor portion of the first product mixture is separated from the liquid portion. A heavy product separator vapor outlet line 73 conveys the separated vapor portion to an F/T reactor condenser 74 where it is further cooled to a temperature in the range of about 5° to 50° C., thereby forming a second product mixture comprising a liquid portion and a gas portion. The liquid portion of the second product mixture contains light hydrocarbon liquids and water. An F/T reactor condenser outlet line 75 conveys the second product mixture to a light product separator 76 where the gas portion of the second product mixture is separated from the liquid portion. A separator tail gas outlet line 77 withdraws the gas portion of the F/T reactor product as a separator tail gas from the top of the light product separator 76 at a rate of about 22,000 to 32,000 m³/hr, a temperature in a range of about 5° to 50° C., and a pressure in a range of about 900 to 1,100 kPa. The separator tail gas comprises nitrogen, carbon monoxide, hydrogen, water and light hydrocarbons typically having a molar composition range of about 90% $N_2$, 5% $CO_2$, 2% CO, 1% $H_2$, 0.5% $H_2O$ and the remainder hydrocarbons. As such, the separator tail gas has a relatively low heating value in the range of about 1,500 to 3,000 kJ/kg.

The separator tail gas outlet line 77 extends from the light product separator 76 to a combustor inlet mixer 78 described hereafter. The separator tail gas outlet line 77 is provided with a tail gas pressure control valve 80 and the separator tail gas heat exchanger 56. The tail gas pressure control valve 80 adjusts the pressure in the light product separator 76 within a range of about 1,500 to 2,800 kPa. The separator tail gas heat exchanger 56 elevates the temperature of the separator tail gas in the separator tail gas outlet line 77 to a range of about 250° to 400° C. using the high-temperature synthesis gas from the ATR outlet line 50 as the heat transfer medium. An excess tail gas line 82 branches from the separator tail gas outlet line 77 downstream of the tail gas pressure control valve 80 and upstream of the separator tail gas heat exchanger 56. The excess tail gas line 82 enables withdrawal of excess separator tail gas from the system 10 during process start-up or in response to process upsets. A flare (not shown) external to the system 10 is provided to dispose of the excess separator tail gas. The flare is accessed through a flare valve 84 in the excess tail gas line 82, preventing the pressure upstream in the separator tail gas outlet line 77 from becoming too high.

The heavy product separator 72 further separates the liquid portion of the first product mixture into the heavy hydrocarbon liquids and water. The light product separator 76 similarly separates the liquid portion of the second product mixture into the light hydrocarbon liquids and water. A heavy hydrocarbon liquid outlet line 85 withdraws the heavy hydrocarbon liquids from the heavy product separator 72 and a light hydrocarbon liquid outlet line 86 withdraws the light hydrocarbon liquids from the light heavy product separator 76. The hydrocarbon liquid outlet lines 85, 86 join to form a common hydrocarbon liquid outlet line 87 mixing the heavy and light hydrocarbon liquids therein, resulting in the recovery of a synthetic hydrocarbon liquid as the desired product of the system 10 at a rate in a range of about 4.3 to 6.6 m³/hr. The synthetic hydrocarbon liquid product preferably has a composition resembling that of a highly paraffinic crude condensate as, for example, represented by the following composition ranges: 10 to 30% LPG, 10 to 20% naphtha, 35 to 65% distillate, 10 to 30% lube stock and 5 to 30% waxes, depending on the catalyst and reactor conditions. The ratio of synthetic hydrocarbon liquid to water in the total liquids recovered from the F/T reactor product is in a range of about 0.75:1 to 1:1.

A first water outlet line 88 withdraws the water from the heavy product separator 72 and a second water outlet line 89 withdraws the water from the light product separator 76 at a combined rate of about 5.1 to 7.8 m³/hr. The water outlet lines 88, 89 convey the water to a pump inlet manifold 90 where they combine with the scrubber water outlet line 64 to form a single water stream exiting the pump inlet manifold 90 via a pump inlet line 92. The pump inlet line 92 conveys the water to a multi-stage centrifugal pump 94 at a rate of about 7.4 to 10.5 m³/hr. The pump 94 elevates the pressure of the water therein to a pressure within a range of about 4,000 to 4,500 kPa and discharges the pressurized water to a pump outlet line 96. The steam conversion heat exchanger 54 is provided in the pump outlet line 96 to heat the pressurized water therein, using the high-temperature synthesis gas from the ATR outlet line 50 as the heat transfer medium. The steam conversion heat exchanger 54 elevates the temperature of the pressurized water to a range of about 300° to 550° C. and at a pressure range of about 4,000 to 4,500 kPa, thereby converting the water in the pump outlet line 96 to steam.

The pump outlet line 96 splits at a junction point 97 downstream of the steam conversion heat exchanger 54 into an ATR steam inlet line 98 and a combustor steam inlet line 100. The ratio of steam fed to the ATR steam inlet line 98 and to the combustor steam inlet line 100 is in a range of about 0.1:1 to 0.4:1. The ATR steam inlet line 98 extends to the ATR carburetor 44 and is provided with an ATR steam flow control valve 104 upstream thereof to adjust the steam flowrate within a range of about 1,250 to 2,700 kg/hr. The ATR carburetor 44 joins the ATR steam inlet line 98, the hydrocarbon feed gas inlet line 34 and an ATR air inlet line 106.

The combustor steam inlet line 100 extends from the junction point 97 to the combustor 30 and is provided with a combustor steam pressure control valve 110 upstream of the combustor 30 to regulate the steam back-pressure within a range of 4,000 to 4,500 kPa. A combustor outlet line 112 conveys a combustor gas/steam mixture formed in the combustor 30 from the combustor 30 to a power turbine inlet gas return manifold 116. The combustor gas/steam mixture typically has a molar composition in a range of about 69 to 72% $N_2$, 0.4 to 4% $O_2$, 5 to 6% $CO_2$, 19 to 24% $H_2O$, and trace oxides of nitrogen. The combustor gas/steam mixture is supplied to the power turbine inlet gas return manifold 116 at a rate of about 55,000 to 67,000 kg/hr, a temperature in a range of about 800° to 1,000° C., and a pressure in a range of about 900 to 1,050 kPa. The power turbine inlet gas return manifold 116 joins the combustor outlet line 112 to the first stage power turbine 22. A cooling air inlet 118 internal to the power turbine 22 conveys cooling air into the power turbine blades and discs (not shown). Accordingly, a combustor gas/steam/air mixture flows through the first stage power turbine 22, and is supplied at a rate in the range of about 55,500 to 70,500 kg/hr, a temperature in a range of about 750° to 1000° C. and a pressure in a range of about 900 to 1,050 kPa. The combustor gas/steam/air mixture is the drive gas for the first stage power turbine 22. The shaft 26 mechanically links the first stage power turbine 22 to the air compressor 18, thereby driving the air compressor 18.

A first stage power turbine outlet 122 conveys spent first stage drive gas from the first stage power turbine 22 to the second stage power turbine 24. The spent first stage drive gas is typically supplied to the second stage power turbine 24 at a rate of about 56,000 to 69,000 kg/hr, a temperature in a range of about 600° to 850° C., and a pressure in a range of about 200 to 400 kPa. The spent first stage drive gas becomes the drive gas for the second stage power turbine 24. The shaft 28 mechanically links the second stage power turbine 24 to the synthesis gas compressor 20, thereby driving the synthesis gas compressor 20. The shaft 28 may also be mechanically linked to an electrical generator (not shown) providing electric power for other on-site uses and/or for export. A second stage power turbine outlet line 124 conveys spent second stage drive gas from the second stage power turbine 24 to a flue 126 at a rate of about 56,000 to 69,000 kg/hr, a temperature in a range of about 400° to 650° C. and a pressure near atmospheric. The flue 126 conveys the spent second stage drive gas and exhausts it from the system 10. The flue gas exhausted from the flue 126 typically has a molar composition of about 69 to 72% $N_2$, 0.5 to 4% $O_2$, 5 to 6% $CO_2$, 19 to 24% $H_2O$ and trace oxides of nitrogen.

The system 10 further comprises an air feed inlet 128 through which an air feed is supplied directly to the air compressor 18. The air feed is typically fed through the air feed inlet 128 at a rate of about 55,000 to 66,000 kg/hr, a temperature of about 15° C. or ambient, and a pressure at about atmospheric. The air compressor 18 compresses the air feed to a pressure in a range of about 850 to 1,050 kPa and a temperature in a range of about 300° to 350° C. An air compressor outlet 130 internal to the air compressor 18 conveys the compressed air feed to a junction point 132 at a rate of about 55,000 to 66,000 kg/hr where the air compressor outlet 130 splits into the cooling air inlet 118 and an air takeoff line 134. The amount of air fed to the cooling air inlet 118 relative to the air takeoff line 134 is in a range of about 1 to 5%. The cooling air inlet 118 conveys its portion of the compressed air feed to the blades and discs of the first stage power turbine 22 as described above. The air takeoff line 134 conveys the remainder of the compressed air feed to a junction point 136 where the air takeoff line 134 splits into the ATR air inlet line 106, a combustion air line 138, and an air bleed line 140. The ratio of air fed to the ATR air inlet line 106 and to the combustion air line 138 is in a range of about 1.25:1 to 2.5:1. The air bleed line 140 normally has no flow therethrough except in the event of an excess pressure build-up in the air takeoff line 134 during start-up, upset conditions or at low feed rates of the hydrocarbon feed gas. The air bleed line 140 is provided with a back pressure control valve 142 connected to an air vent 144 should such an excess pressure build-up in the air take-off line 134 occur.

The combustion air line 138 extends from the first air junction point to a second air junction point 146 where the combustion air line 138 splits into a primary air combustor inlet line 148 and a secondary air combustor inlet line 150. The primary air combustor inlet line 148 is provided with a primary air flow control valve 152 to adjust the primary air flow rate in the line 148 from about 13,000 to 21,000 kg/hr, thereby providing a sufficient air feed to maintain combustion within the combustor 30. The secondary air combustor inlet line 150 is likewise provided with a secondary air flow control valve 156 to adjust the secondary air flow rate in the line 150. The combustor inlet mixer 78 joins the primary combustor air inlet line 148 with the separator tail gas outlet line 77 to mix the gas streams of the lines 148 and 77 therein. A combustor inlet burner assembly 154 exits the combustor inlet mixer 78 and extends into the combustor 30. The combustor inlet burner assembly 154 injects the gaseous mixture of the primary air feed and separator tail gas, termed the combustor feed gas, to the combustor 30 for combustion therein. The combustor feed gas typically has a molar composition in a range of about 86 to 87% $N_2$, 6 to 7% $O_2$, 3% $CO_2$, 1% CO, 0.5 to 1% $H_2$, 0.2% $H_2O$ and the remainder methane and heavier hydrocarbons, and is fed to the combustor 30 at a rate of about 32,000 to 48,000 ma/hr, a temperature in a range of about 250° to 350° C., and a pressure in a range of about 900 to 1,050 kPa. The secondary air combustor inlet line 150 conveys the secondary air feed for injection into the combustor 30. The secondary air feed oxidizes the remainder of the combustibles in the combustor 30, while diluting and cooling the combustor gas/steam/air mixture exiting the combustor to the power turbine inlet manifold 116. The combustor gas/steam/air feed is cooled to a temperature below the maximum temperature allowable in the first stage power turbine 22, typically in a range of about 800° to 1000° C. depending on the metallurgy of the turbine 22. The combustor 30 is a high temperature vessel typically maintained at a temperature range of about 870° to 1,200° C., and a pressure range of about 900 to 1,050 kPa. The combustor 30 may contain a catalyst to promote the combustion reactions therein.

The ATR air inlet line 106 extends from the junction point 136 to the ATR carburetor 44 described above and conveys its remaining portion of the remaining compressed air feed to the ATR carburetor 44. The ATR air inlet line 106 is provided with an ATR air inlet flow control valve 158 to vent the air feed from the line 106, thereby adjusting the air flowrate in the line 106 within a range of about 30,500 to 52,500 kg/hr.

Figure 2:
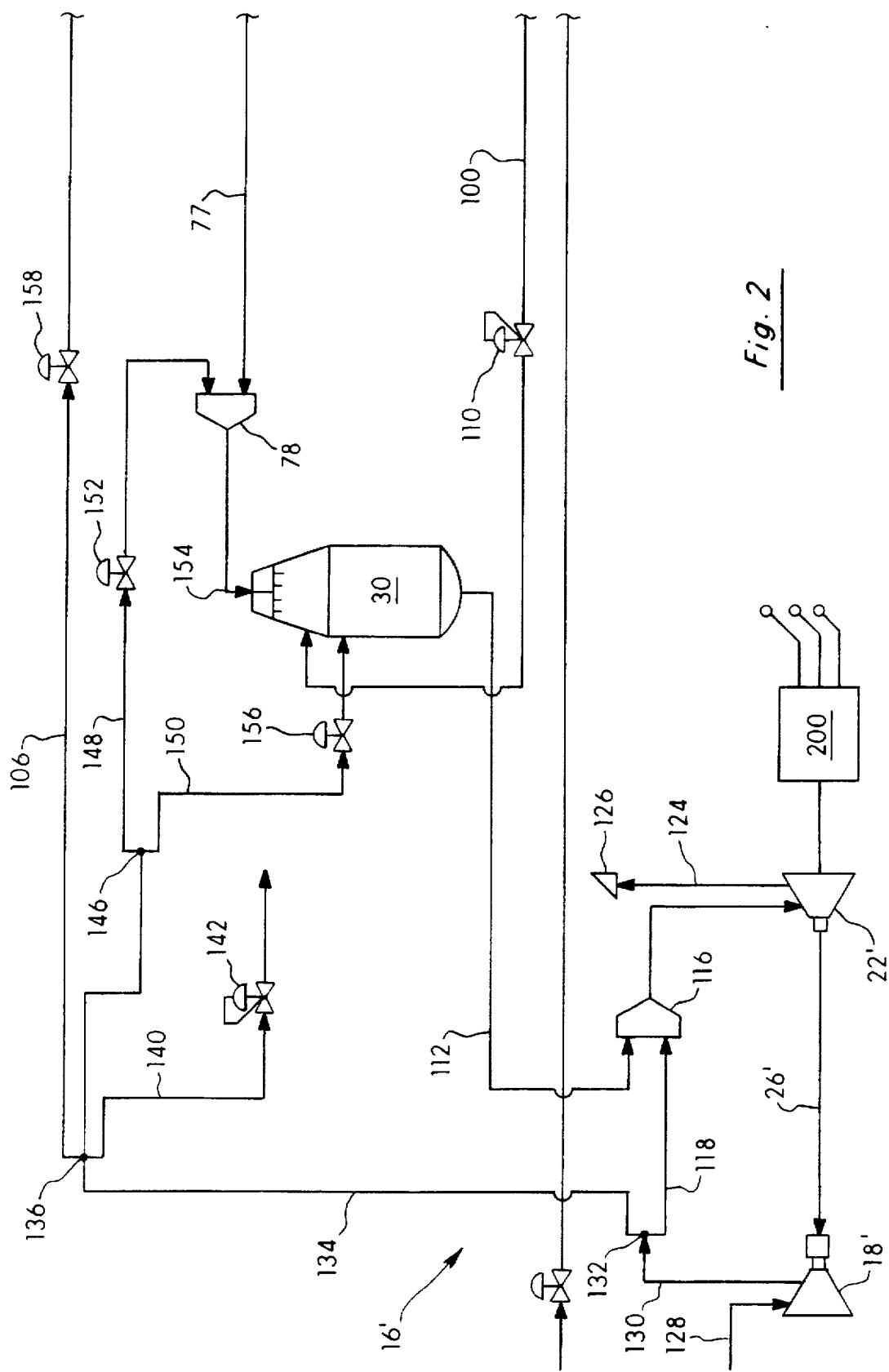

Referring to FIG. 2, an alternate embodiment of the present invention is shown. The embodiment of FIG. 2 is essentially the same as the embodiment of FIG. 1 with the exception of modifications to the Brayton cycle. Accordingly, FIG. 2 shows essentially only the Brayton cycle of a hydrocarbon gas conversion system, the remainder of the system being substantially the same as the system 10 of FIG. 1. The Brayton cycle of FIG. 2 is generally designated 16'. The remaining components of the system shown in FIG. 2 that are common to both the embodiments of FIGS. 1 and 2 are designated by common reference characters. The Brayton cycle 16' comprises a single power turbine 22' linked by a single shaft 26' to both an air compressor 18' and an electrical generator 200. The electrical generator 200 provides electric power to an electric motor (not shown) that drives the synthesis gas compressor and also provides electric power for export. As in the Brayton cycle 16 of FIG. 1, the combustor outlet line 112 conveys the combustion gas/steam/air mixture formed in the combustor from the combustor 30 to the power turbine inlet gas return manifold 116 that joins the combustor outlet line 112 to the power turbine 22'. Although not shown, still further embodiments of the present invention having alternate Brayton cycle configurations are within the purview of the skilled artisan applying the foregoing teaching. As such, these embodiments fall within the scope of the present invention.

It is also apparent to the skilled artisan that many alternatives are available within the scope of the present invention for selecting specific components having utility in the Brayton cycles described herein. In particular, it is most practical to exploit and utilize commercially available gas-turbine engine packages. Commercial gas-turbine engine packages are commonly used to generate electric power or to drive industrial compressors or pumps. Commercial gas-turbine engine packages are also used for motive applications such as powering ships. As such, commercial packages are available in many designs and sizes. It is advantageous to select a package design and size that most closely matches the particular requirements of the given application. Thus, in the system 10 of FIG. 1, the size of the gas-turbine package is preferably selected based on the volume of gas available for conversion to liquid products.

It is also noted that different designs of commercial gas-turbine engine packages operate at significantly different pressures and efficiencies. Since the reactions that occur in the ATR and F/T reactor are not significantly influenced by the reactor pressure, with the exception of carbon or soot formation in the ATR that is more likely to occur at higher pressures, it is advantageous to select process pressure conditions that best utilize a particular gas-turbine package size and design. For example, a commercially available gas-turbine engine package sized for an air feed mass flowrate of 66,000 kg/hr and a pressure ratio of 10 over atmospheric is determined to be suitable for the hydrocarbon gas conversion system 10 of FIG. 1 having a hydrocarbon feed gas rate of about 8,000 to 12,000 $m^3/hr$. Based on this particular gas-turbine engine package, the operating pressure of the ATR and combustor is selected in a range of about 950 to 1,050 kPa. The pressure ratio of the synthesis gas compressor is then determined based on the pressure drop across the system and the requirement to return the tail gas to the combustor at a pressure of about 950 to 1,050 kPa.

Gas-turbine engines operating at lower pressures (300 to 1,100 kPa) may employ a "recuperator" design, wherein the gas-turbine engine is mechanically configured to draw off compressed air for preheating in an external heat exchanger heated with waste heat from the engine exhaust prior to returning the air to the combustor. In power production applications, less fuel is required to produce a given amount of power using the recuperator design. Gas-turbine packages employing a recuperator design can be adapted for the system of the present invention by utilizing the take-off and return nozzles on the gas-turbine engine. Some gas-turbine packages are designed with integral external combustors or are designed to accommodate separate external combustors. A gas-turbine package utilizing an external combustor has been found to be the most practical for use in the present system 10 with a minimum of mechanical modification. Such gas-turbine packages also minimize the size of the gas-turbine engine required.

Referring to FIG. 3, another alternate embodiment of the present invention is shown. The embodiment of FIG. 3 is essentially the same as the embodiment of FIG. 1, again with the exception of modifications to the Brayton cycle. Accordingly, FIG. 3 shows essentially only the Brayton cycle of a hydrocarbon gas conversion system, the remainder of the system being substantially the same as the system 10 of FIG. 1. The Brayton cycle of FIG. 3 is generally designated 16". The remaining components of the system shown in FIG. 3 that are common to both the embodiments of FIGS. 1 and 3 are designated by common reference characters. The Brayton cycle 16" of the present embodiment includes a pair of compressors 18", 20", a pair of power turbines 22", 24" mechanically linked by shafts 26", 28" to the compressors 18", 20", respectively, and a combustor 300 that is internal to the first stage power turbine 22". For clarity, the internal combustor 300 is shown conceptually apart from the power turbine 22", but it is understood that the combustor 300 is integral therewith. The design of the present gas-turbine engine employs a compact, internal, light-weight, air-cooled combustor or several smaller internal combustors in parallel, rather than an external combustor. Such engines are somewhat similar in design to those used for powering aircraft.

The present gas-turbine engine operates at a substantially larger capacity than the above-recited embodiments with relatively high air flowrates throughout the system because large amounts of cooling air are required to cool the internal combustor 300. Many of the distinctions between this embodiment and the above-recited embodiments are attributable to the increased air cooling load of the internal combustor 300.

In operation of the Brayton cycle 16", the air feed inlet 128 delivers an air feed to the air compressor 18" where it is compressed and conveyed through the air takeoff line 134 to a junction point 136 where the air takeoff line 134 splits four ways. A portion of the compressed air feed continues to the ATR through the ATR air inlet line 106. Another portion of the compressed air feed is conveyed via the combustion air line 138 to the burner nozzle 302 of the combustor 300 where the compressed air feed is mixed with the other combustor inlet gases, including the tail gas from the separator tail gas outlet line 77 and process steam from the power turbine steam line 100, before being injected into the combustor 300 through the combustor inlet 304. The combustor 300 may contain a catalyst, such as a metal oxide or a noble metal (e.g. platinum), to promote the combustion reactions therein. Still another portion of the compressed air feed is conveyed to the first stage power turbine 22" via the cooling air inlet line 118" where the compressed air feed cools the power turbine disk and blades and is mixed with the combustion gases from the combustor 300 and the combustor cooling air. The final portion of the compressed air feed is circulated via a combustor cooling air line 306 through an annular combustor cooling shroud 308 to dissipate the combustor heat 310 and cool the combustor 300 via air-film cooling of the metal walls of the combustor 300. The gases exiting the power turbine inlet gas return manifold 116" drive the first stage power turbine 22". In all other respects the Brayton cycle 16" operates in substantially the same manner as the Brayton cycle 16 of FIG. 1.

It is noted that engines having an internal air-cooled combustor design require a larger capacity to convert a given amount of a hydrocarbon feed gas than an engine alternately designed to accommodate an external combustor having a refractory lining for heat protection. Nevertheless, the lower cost and wider commercial availability of engines having an internal air-cooled combustor design for a given capacity or for a minimum size requirement in a particular application may favor selection of such engines. In applications where a market or a need exists for a significant amount of excess power beyond that required to operate the hydrocarbon gas conversion system, high-pressure engines having an aero-derivative design may be advantageous because of their enhanced ability to generate excess power.

While the foregoing preferred embodiments of the invention have been described and shown, it is understood that alternatives and modifications, such as those suggested and others, may be made thereto and fall within the scope of the present invention.

I claim:

1. A process for converting a lighter hydrocarbon gas to heavier hydrocarbons comprising:
  a) reacting an air feed and a lighter hydrocarbon feed gas in a first reactor to produce a synthesis gas comprising hydrogen and carbon monoxide;
  b) feeding said synthesis gas to a second reactor containing a hydrocarbon synthesis catalyst and reacting said synthesis gas in the presence of said hydrocarbon synthesis catalyst to produce heavier hydrocarbons, a dilute tail gas and water, wherein said dilute tail gas contains at least about 90 mole percent inert non-combustible components;
  c) feeding said dilute tail gas to a combustor and combusting said dilute tail gas in said combustor to produce a combustion gas;
  d) driving a power turbine with said combustion gas; and
  e) driving an air compressor with said power turbine to compress said air feed to said first reactor.

2. The process of claim 1 further comprising heating said water with said synthesis gas to produce process steam.

3. The process of claim 2 further comprising feeding a portion of said process steam to said combustor.

4. The process of claim 2 further comprising feeding a portion of said process steam to said first reactor.

5. The process of claim 1 further comprising feeding a portion of said air feed to said power turbine.

6. The process of claim 1 further comprising feeding a portion of said air feed to said combustor having a burner.

7. The process of claim 6 wherein said portion of said air feed is split into a primary feed and a secondary feed, said primary feed fed to said combustor upstream of said burner and said secondary feed fed to said combustor downstream of said burner.

8. The process of claim 1 further comprising heating said dilute tail gas with said synthesis gas upstream of said combustor to increase the flame temperature of said dilute tail gas upon combustion in said combustor.

9. The process of claim 1 further comprising heating said lighter hydrocarbon feed gas with said synthesis gas.

10. The process of claim 1 wherein said power turbine is a first power turbine, said process further comprising driving a second power turbine with said combustion gas and wherein said second power turbine is positioned in series with said first power turbine.

11. The process of claim 10 further comprising driving a synthesis gas compressor with said second power turbine to compress said synthesis gas fed to said second reactor.

12. The process of claim 10 further comprising driving an electrical generator with said second power turbine to generate electric power.

13. The process of claim 1 wherein said combustor is external to said power turbine.

14. The process of claim 1 wherein said combustor is internal to said power turbine.

15. The process of claim 1 wherein said inert non-combustible components of said dilute tail gas include nitrogen.

16. The process of claim 1 further comprising driving an electrical generator with said power turbine to generate electric power and driving an electric motor with said electric power.

17. The process of claim 16 further comprising driving a synthesis gas compressor with said electric motor to compress said synthesis gas to said second reactor.

18. A process for converting a lighter hydrocarbon gas to heavier hydrocarbons comprising:
  a) reacting a gaseous mixture comprising an air feed and a lighter hydrocarbon feed gas to produce a synthesis gas comprising hydrogen and carbon monoxide;
  b) reacting said synthesis gas in the presence of a hydrocarbon synthesis catalyst to produce heavier hydrocarbons, a dilute tail gas and water, wherein said dilute tail gas contains at least about 90 mole percent inert non-combustible components;
  c) preheating said dilute tail gas with said synthesis gas and combusting said dilute tail gas at an increased flame temperature to produce a combustion gas;

d) generating mechanical power with said combustion gas; and e) compressing said air feed with said mechanical power.

19. The process of claim 18 further comprising heating said water with said synthesis gas to produce process steam.

20. The process of claim 19 wherein said dilute tail gas is combusted in the presence of said process steam.

21. The process of claim 18 wherein said dilute tail gas is combusted with a portion of said air feed.

22. The process of claim 18 further comprising heating said lighter hydrocarbon feed gas with said synthesis gas.

23. The process of claim 18 further comprising compressing said synthesis gas with said mechanical power.

24. The process of claim 18 further comprising generating electric power with said mechanical power.

25. The process of claim 24 further comprising compressing said synthesis gas with said electric power.

26. The process of claim 18 wherein said inert non-combustible components of said dilute tail gas include nitrogen.

27. A process for converting a lighter hydrocarbon gas to heavier hydrocarbons comprising:

a) reacting a gaseous mixture comprising a first portion of an air feed and a lighter hydrocarbon feed gas to produce a synthesis gas comprising hydrogen and carbon monoxide;

b) reacting said synthesis gas in the presence of a hydrocarbon synthesis catalyst to produce heavier hydrocarbons, a dilute tail gas and water, wherein said dilute tail gas contains at least about 90 mole percent inert non-combustible components;

c) combusting said dilute tail gas with a second portion of said air feed to produce a combustion gas;

d) generating mechanical power with said combustion gas; and e) compressing said first and second portions of said air feed with said mechanical power.

28. The process of claim 27 further comprising heating said water to produce process steam and combusting said dilute tail gas in the presence of said process steam.

29. The process of claim 27 further comprising heating said lighter hydrocarbon feed gas with said synthesis gas.

30. The process of claim 27 further comprising compressing said synthesis gas with said mechanical power.

31. The process of claim 27 further comprising generating electric power with said mechanical power.

32. The process of claim 31 further comprising compressing said synthesis gas with said electric power.

33. A process for converting a lighter hydrocarbon gas to heavier hydrocarbons comprising:

a) reacting a gaseous mixture comprising an air feed a lighter hydrocarbon feed gas to produce a synthesis gas comprising hydrogen and carbon monoxide;

b) reacting said synthesis gas in the presence of a hydrocarbon synthesis catalyst to produce heavier hydrocarbons, a dilute tail gas and water, wherein said dilute tail gas contains at least about 90 mole percent inert non-combustible components;

c) heating said water to produce process steam;

d) combusting said dilute tail gas in the presence of said process steam to produce a combustion gas;

e) generating mechanical power with said combustion gas; and f) compressing said air feed with said mechanical power.

34. The process of claim 33 further comprising heating said lighter hydrocarbon feed gas with said synthesis gas.

35. The process of claim 33 further comprising compressing said synthesis gas with said mechanical power.

36. The process of claim 33 further comprising generating electric power with said mechanical power.

37. The process of claim 36 further comprising compressing said synthesis gas with said electric power.

38. The process of claim 1 wherein the remainder of said dilute tail gas includes combustible components.

39. The process of claim 38 wherein said combustible components include hydrogen, carbon monoxide and hydrocarbons.

40. The process of claim 18 wherein the remainder of said dilute tail gas includes combustible components.

41. The process of claim 40 wherein said combustible components include hydrogen, carbon monoxide and hydrocarbons.

* * * * *

UNITED STATES PATENT AND TRADEMARK OFFICE
CERTIFICATE OF CORRECTION

PATENT NO. : 5,733,941
DATED : March 31, 1998
INVENTOR(S) : John J. Waycuilis

It is certified that error appears in the above-indentified patent and that said Letters Patent is hereby corrected as shown below:

Col. 11, line 5: Delete "ma/hr." and insert -- $m^3/hr$, --.

Signed and Sealed this

Eighth Day of September, 1998

Attest:

BRUCE LEHMAN

Attesting Officer     Commissioner of Patents and Trademarks